United States Patent
Reed et al.

(10) Patent No.: US 8,870,826 B2
(45) Date of Patent: Oct. 28, 2014

(54) COMBINED OTIC ASPIRATOR AND MEDICATION DISPENSER

(75) Inventors: Don C. Reed, Randolph, NJ (US); Chris Sakezlesa, Sarasota, FL (US)

(73) Assignee: Auris Medical LLC, Freehold, NJ (US)

( * ) Notice: Subject to any disclaimer, the term of this patent is extended or adjusted under 35 U.S.C. 154(b) by 2285 days.

(21) Appl. No.: 11/597,400

(22) PCT Filed: May 24, 2005

(86) PCT No.: PCT/US2005/018422
§ 371 (c)(1),
(2), (4) Date: Nov. 22, 2006

(87) PCT Pub. No.: WO2005/115527
PCT Pub. Date: Dec. 8, 2005

(65) Prior Publication Data
US 2007/0167918 A1    Jul. 19, 2007

Related U.S. Application Data

(60) Provisional application No. 60/573,795, filed on May 24, 2004.

(51) Int. Cl.
| | |
|---|---|
| *A61M 5/00* | (2006.01) |
| *A61M 3/02* | (2006.01) |
| *A61F 11/00* | (2006.01) |
| *A61M 1/00* | (2006.01) |
| *A61B 1/227* | (2006.01) |

(52) U.S. Cl.
CPC ...... *A61F 11/002* (2013.01); *A61M 2210/0662* (2013.01); *A61M 3/0254* (2013.01); *A61M 1/0003* (2013.01); *A61B 1/227* (2013.01); *A61M 1/0064* (2013.01)
USPC .......................................... 604/187; 604/500

(58) Field of Classification Search
USPC ......... 604/187, 188, 191, 206, 232, 234, 259, 604/500–505; 606/132
See application file for complete search history.

(56) References Cited

U.S. PATENT DOCUMENTS

| | | | |
|---|---|---|---|
| 1,950,137 A | | 3/1934 | Dowe |
| 4,367,737 A | | 1/1983 | Kozam et al. |
| 4,609,737 A | | 9/1986 | Hirata et al. |
| 4,610,666 A | | 9/1986 | Pizzino |
| 4,766,886 A | * | 8/1988 | Juhn .............................. 600/200 |
| 4,790,823 A | * | 12/1988 | Charton et al. ............... 604/136 |
| 5,174,475 A | | 12/1992 | Day et al. |
| 5,354,284 A | * | 10/1994 | Haber et al. .................. 604/191 |
| 5,380,286 A | | 1/1995 | van den Haak |
| 5,665,094 A | * | 9/1997 | Goldenberg ................... 606/109 |
| 5,916,150 A | * | 6/1999 | Sillman ......................... 600/184 |
| 6,024,726 A | * | 2/2000 | Hill ............................... 604/187 |

(Continued)

Primary Examiner — Kevin C Sirmons
Assistant Examiner — Phillip Gray
(74) Attorney, Agent, or Firm — Hedman & Costigan, P.C.; James V. Costigan; Kathleen A. Costigan

(57) ABSTRACT

A device for making an incision in the tympanic membrane, withdrawing fluid from the tympanic cavity and administering a medicament to the space behind the tympanic membrane is provided. The device has a barrel-shaped casing (1) having a rotatable end turret (38). A first trigger (2) allows a shaft (18) to pierce the tympanic membrane and a tubular vacuum cartridge (32). The cartridge allows aspiration of fluid. A second trigger (4) causes medicament (34) to be released into the space behind the tympanic membrane.

11 Claims, 6 Drawing Sheets

(56) References Cited

U.S. PATENT DOCUMENTS

| | | |
|---|---|---|
| 6,059,803 A | 5/2000 | Spilman |
| 6,423,050 B1 | 7/2002 | Twardowski |
| 6,440,102 B1 | 8/2002 | Arenberg et al. |
| 6,578,581 B1 | 6/2003 | Khalsa |

* cited by examiner

COMBINED OTIC ASPIRATOR AND MEDICATION DISPENSER

FIELD OF THE INVENTION

The invention provides a novel apparatus and method for the treatment of middle ear infections.

BACKGROUND OF THE INVENTION

Apparatus are known for use in connection with the middle and inner ear where the apparatus is capable of (1) delivering various liquids and solids to the inner ear structures; (2) extracting, withdrawing, or exchanging fluid materials from the inner ear; (3) transferring fluid materials into and out of the inner ear via the round window membrane so that items [1] and [2] can be accomplished; (4) enabling middle and inner ear structures to be electrophysiologically monitored using electrocochleography ("ECoG") procedures; (5) altering the permeability of the round window membrane in the ear for a variety of therapeutic purposes with drugs, chemical agents, or iontophoresis; and (6) creating a discrete sealed or non-sealed "fluid-receiving zone" within the round window niche so that fluid materials can be transferred into and out of the inner ear via the adjacent round window membrane in a controlled and site-specific manner.

In order to treat ear disorders, it has been necessary to deliver therapeutic agents to various ear tissues in a controlled, safe, and efficient manner. For example, a variety of structures have been developed which are capable of delivering/administering therapeutic agents into the external auditory canal of the outer ear. U.S. Pat. No. 4,034,759 to Haerr discloses a hollow, cylindrical tube manufactured of sponge material (e.g. dehydrated cellulose) which is inserted into the external auditory canal of a patient. When liquid medicines are placed in contact with the tube, it correspondingly expands against the walls of the auditory canal. As a result, accidental removal of the tube is prevented. Furthermore, medicine materials absorbed by the tube are maintained in contact with the walls of the external auditory canal for treatment purposes. Other absorbent devices designed for treatment of the external auditory canal and related tissue structures are disclosed in U.S. Pat. No. 3,528,419 to Joechle, U.S. Pat. No. 4,159,719 to Haerr, and U.S. Pat. No. 2,642,065 Negri. The Negri patent specifically describes a medicine delivery device with an internally-mounted, frangible medicine container which, when broken, releases liquid medicines into an absorbent member.

However, the delivery of therapeutic agents in a controlled and effective manner is considerably more difficult with respect to tissue structures of the inner ear (e.g. those portions of the ear surrounded by the otic capsule bone and contained within the temporal bone which is the most dense bone tissue in the entire human body). The same situation exists in connection with tissue materials which lead into the inner ear (e.g. the round window membrane). Exemplary inner ear tissue structures of primary importance for treatment purposes include but are not limited to the cochlea, the endolymphatic sac/duct, the vestibular labyrinth, and all of the compartments (and connecting tubes) which include these components. Access to the above-described inner ear tissue regions is typically achieved through a variety of structures, including but not limited to the round window membrane, the oval window/stapes footplate, the annular ligament, the otic capsule/temporal bone, and the endolymphatic sac/endolymphatic duct, all of which shall be considered "middle-inner ear interface tissue structures" as described in greater detail below. In addition, as indicated herein, the middle ear or tympanic cavity shall be defined as the physiological air-containing tissue zone behind the tympanic membrane (e.g. the ear drum) and proximal to the inner ear.

The inner ear tissues listed above are of minimal size and only readily accessible through microsurgical procedures. In order to treat various diseases and conditions associated with inner ear tissue the delivery of medicines to such structures is often of primary importance. Representative medicines which are typically used to treat inner ear conditions include but are not limited to urea, mannitol, sorbitol, glycerol, lidocaine, xylocaine, epinephrine, immunoglobulins, sodium chloride, steroids, heparin, hyaluronidase, aminoglycoside antibiotics (streptomycin/gentamycin), antioxidants, neurotrophins, nerve growth factors, various therapeutic peptides, and polysaccharides. Of particular interest in this list are compounds which are used to alter the permeability of the round window membrane within the ear using, for example, hyaluronidase and iontophoretic techniques (defined below). Likewise, treatment of inner ear tissues and/or fluid cavities may involve altering the pressure, volume, electrical activity, and temperature characteristics thereof. Specifically, a precise balance must be maintained with respect to the pressure of various fluids within the inner ear and its associated compartments. Imbalances in the pressure and volume levels of such fluids can cause various problems, including but not limited to conditions known as endolymphatic hypertension, perilymphatic hypertension, perilymphatic fistula, intracochlear fistula, Meniere's disease, tinnitus, vertigo, hearing loss related to hair cell or ganglion cell damage/malfunction, and ruptures in various membrane structures within the ear.

Of further interest regarding the delivery of therapeutic agents to the middle ear, inner ear, and middle-inner ear interface tissue structures are a series of related and co-owned patents, namely, U.S. Pat. Nos. 5,421,818; 5,474,529, and 5,476,446 all to Arenberg. Each of these patents discloses a medical treatment apparatus designed to deliver fluid materials to internal ear structures. U.S. Pat. No. 5,421,818 describes a treatment system which includes a tubular stem attached to a reservoir portion with an internal cavity designed to retain a supply of therapeutic fluid compositions therein. The side wall of the reservoir portion further comprises fluid transfer means (e.g. pores or a semi-permeable membrane). Contact between the fluid transfer means and the round window membrane in a patient allows fluid materials to be delivered on-demand to the round window membrane, followed by diffusion of the fluid materials through the membrane into the inner ear. U.S. Pat. No. 5,474,529 involves a therapeutic treatment apparatus with a plurality of reservoir portions (e.g. a first and a second reservoir portion in a preferred embodiment) which are connected to multiple tubular stems that are designed for implantation into the endolymphatic sac and duct using standard microsurgical techniques. Finally, U.S. Pat. No. 5,476,446 discloses a therapeutic treatment apparatus which includes a reservoir portion for retaining liquid medicine materials therein, a first tubular stem on one side of the reservoir portion, and a second tubular stem on the opposite side of the reservoir portion. The second stem is designed to reside within the external auditory canal of a patient lateral to the ear drum, while the first stem is sired for placement within an opening formed in the stapes footplate/annular ligament so that medicine materials in fluid form can be delivered into the inner ear from the reservoir portion (which resides in the middle ear cavity medial to the ear drum).

A different approach for transferring materials into and out of the inner ear via the round window membrane/round window niche is disclosed in U.S. patent application Ser. No. 08/874,208 filed on Jun. 13, 1997. This application describes a system in which one or more fluid transfer conduits are provided which are operatively connected to a "cover member" that is designed for placement on top of the niche (e.g. at its point of entry) or within the niche. The cover member is used to create a "fluid-receiving zone" (or "inner ear fluid transfer space") which is partially or entirely sealed in order to facilitate fluid transfer into and out of the inner ear. In one embodiment, the cover member consists of a thin, solid, plate-like structure that is secured in position on top of the niche at its point of entry as previously noted. Alternatively, the cover member may comprise a portion of flexible and compressible material which, during placement within the round window niche, is compressed and thereafter allowed to expand once the portion of compressible material is positioned within the niche. As a result, the cover member can engage the internal side wall of the round window niche, thereby creating the fluid-receiving zone ("inner ear fluid transfer space") between the compressible cover member and the round window niche. Representative materials used to construct the portion of compressible material associated with the cover member in this particular embodiment optimally involve foam-type products including but not limited to polyethylene foam, polyether foam, polyester foam, polyvinyl chloride foam, polyurethane foam, and sponge rubber (e.g. synthetic or natural), all of which are of the closed cell variety, with such materials being non-fluid-absorbent in accordance with the substantial lack of open cells therein. Specifically, the non-fluid-absorbent character of these materials results from the closed cell structure thereof which prevents fluid materials from being absorbed compared with open cell (absorbent) foam products.

The present invention represents an advance in the art of middle ear or tympanic cavity treatment, diagnosis, and medicine delivery as described in detail below. In part, the prior art treatment of acute middle ear infections has been based on tympanocentisis or insertion of tubes into the tympanum or tapping the ear with a conventional syringe or a aspirator. Aspirators are known which are adapted to apply suction using a vacuum which is based on an externally provided vacuum source or a vacuum that is generated by the withdrawal of a piston in the aspirator device. Generally, the use of surgical intervention has been accompanied with the evacuation of fluid in conjunction with the systemic administration of antimicrobial medicaments to treat the localized infection in the ear.

The present invention is concerned with providing a novel apparatus and method of treating middle ear infections that is capable of rapidly (a) making a surgical incision in the tympanum; (b) aspirating fluid from the behind the tympanum and (c) administering a dose of an antimicrobial compound using a compact handheld apparatus.

SUMMARY OF THE INVENTION

The apparatus of the invention comprises a device having a barrel shaped casing having rotatable ends adapted to engage tubular elements:

(a) a first actuating trigger which activates a first tubular element comprising a spring-loaded, hollow piercing shaft having a first end which is adapted to penetrate a tympanic membrane when it is extended from said barrel shaped casing by the action of said spring and a second internal end which is adapted to engage an end of a tubular vacuum container having a frangible seal;

(b) said tubular vacuum container having a frangible seal, being positioned in said barrel shaped casing and being spring loaded for axial rotation in said barrel with a first axial spring, when said hollow piercing shaft is extended from said barrel casing, said tubular vacuum container having a frangible seal, being adapted to axially move into register with said second internal end of said piercing shaft, said piercing shaft being adapted to break said frangible seal as said tubular vacuum container moves into register with said second end of said hollow piercing shaft to expose said hollow piercing element to the effect of vacuum in said tubular vacuum container in order to aspirate fluid from said tympanic cavity or middle ear;

(c) a second trigger actuating axial spring loaded pressurized tubular medicament chamber, which is positioned in said barrel casing and is adapted to rotate under the action of said second trigger and engage the second internal end of said piercing element and release medicament into the space behind the tympanic membrane.

Accordingly, it is a primary object of the invention to provide an apparatus which is capable of rapidly (a) making an incision in the tympanic membrane; (b) evacuating the fluid contents; and (c) administering a medicament to treat any pathology behind the tympanic membrane.

These and other objects will become apparent from a review of the Detailed Description of the Invention.

DETAILED DESCRIPTION OF THE INVENTION

Figure 1:
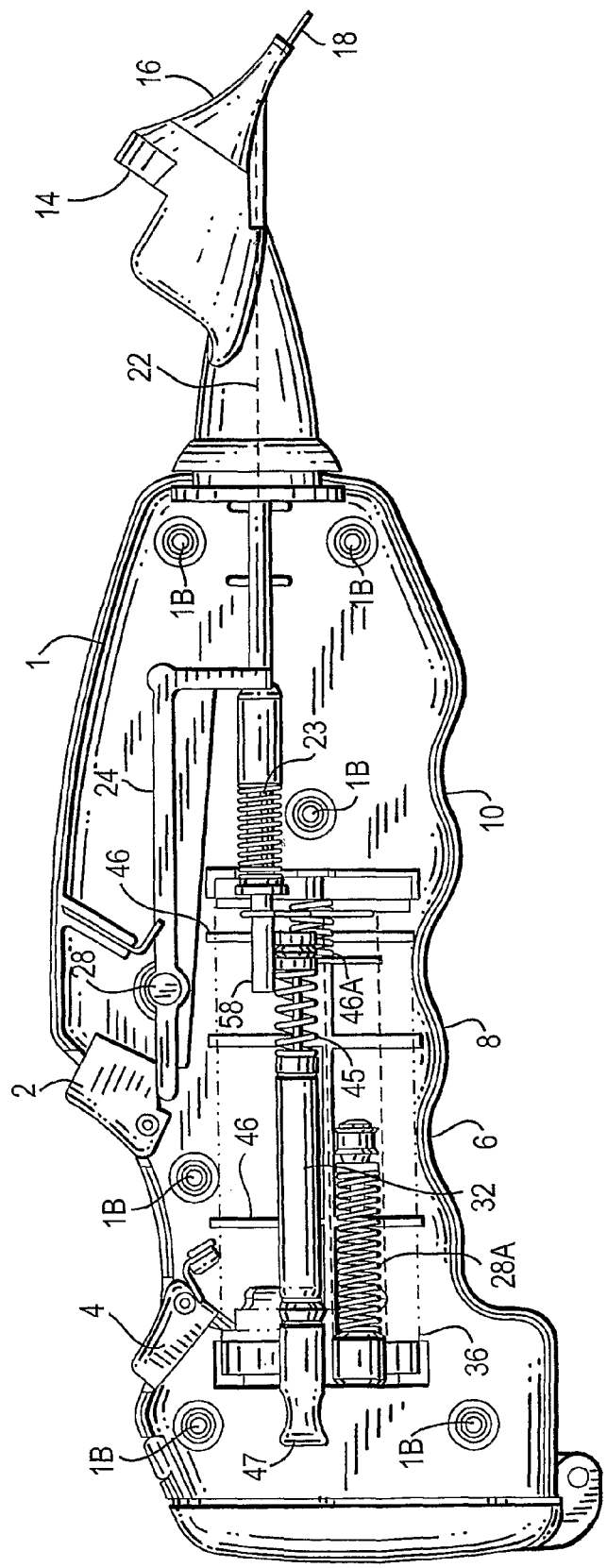
FIG. 1 is a cutaway view of the apparatus of the invention which shows one side of the cover removed.

As best seen in FIG. 1, the apparatus of the invention comprises an external cover 1 having two halves held together by rivets placed in rivet holes 1B. A first actuating trigger 2 and a second actuating trigger 4 are mounted on the cover. The cover 1 is provided with a plurality of indentations 6, 8 and 10 that serve as ergonomically shaped finger gripping surfaces. At the forward end 12 of the apparatus, a viewing opening 14 is provided that is adapted to engage a standard otoscope 12 (in FIG. 2). At the tip 14 of the viewing cannula 16, the needle 18 is shown in a partially extended position as if it was being extended for the purpose of piercing the tympanic membrane.

The viewing opening 14 is preferably arranged so that it allows the physician to view the tympanic membrane as the needle 18 pierces the tympanic membrane. As shown in FIG. 1, the partially extended needle 18 follows the path shown by dotted line 22 as it is extended by the spring 23 which is controlled by latch 24 that pivots at mounting pivot 28 when first actuating trigger 2 is depressed. Spring band 19 provides a resistance that holds trigger 2 in the open position. Needle 18 is preferably made of a resilient material such as a polyimide that is flexible enough to bend as it is passed through an internal channel shown by dotted line 22 in viewing cannula 16. The needle cartridge assembly 30, vacuum cartridge 32 and medicament chamber 34 are shown within barrel 36 which is shown within cover 1 by dotted lines. Barrel 36 is a cylindrical structure provided with a space 36B that receives the needle cartridge assembly 30 and separate chambers for the vacuum cartridge 32 and the medicament chamber 34.

The barrel 36 comprises a cylindrical structure which is divided into a hollow first chamber 36B and an offset core of solid material that has two separate chambers. The first chamber acts as a mounting means for vacuum cartridge 32 and the second chamber is medicament chamber 34.

Dotted lines 34C on barrel 36 show the position of medicament chamber 34 that houses the medicament and its associated delivery elements which comprise a spring, a plunger element and a seal which engages end 58 of needle retainer element 44A when barrel 36 is rotated into position for ejecting medicament. Dotted lines 32C show the position in barrel 36 where vacuum cartridge 32 is placed. End cap 60, which allows access to the inside of the cover 1 is mounted at the end of cover 1 opposite the end on which tip 14 is mounted, on a movable axle 62 and is held in a closed position with locking tab 64.

Figure 2:
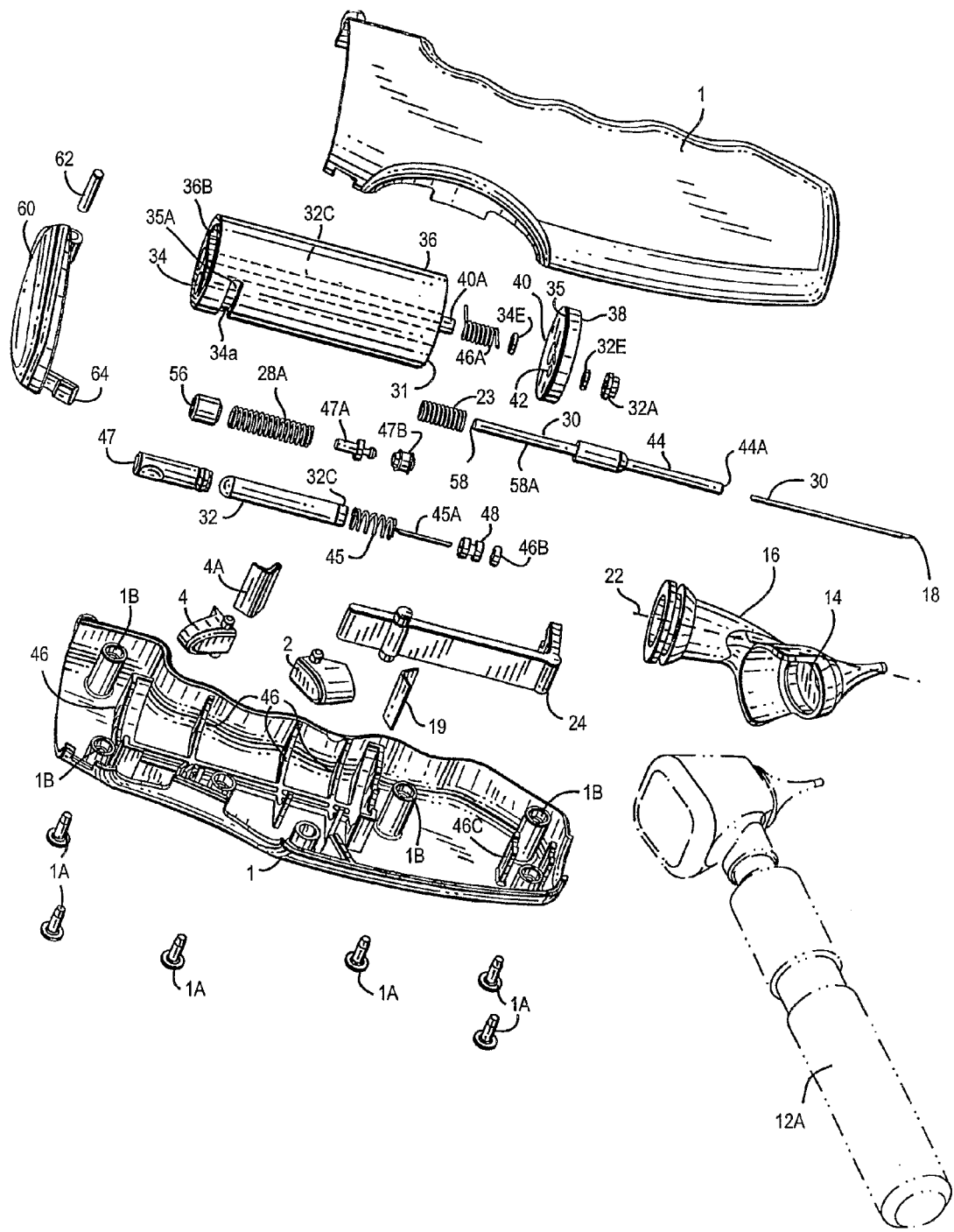
FIG. 2 is a partially exploded view of the apparatus of the invention which shows the cover sections and the operating components.

As best seen in FIG. 2, a partially exploded view of the otic aspirator/dispenser of FIG. 1 is disclosed which has a view of otoscope 12A which may be placed in opening 14 of cannula 16. At the forward end 31 of the barrel 36 is a turret 38 which has an axially located opening 40 and remains fixed while the barrel 36 is rotated from a first position where the needle assembly is in register with an off center hole 42 in turret 38 that allows the needle to be extended from the barrel by the action of spring 23. The barrel 36 is mounted within cover 1 on complimentary molded half circle shaped supports 46 which are on the inside of both cover halves but are only shown on one side of cover 1 in FIG. 2.

The forward end 31 of the barrel 36 has an opening into space 36B and is also provided with an axle 40A which is fitted into hole 40 in turret 38. Opening 30B is provided to allow the shaft 58A below needle retainer element 44A to move out of the barrel 36 when trigger 2 is activated. Opening 32D is provided to allow vacuum cartridge 32 to communicate with the end 58 of needle cartridge assembly 30 when barrel 36 is rotated by spring 46A. O-ring 32E is placed in recess 32F to provide a seal between opening 32D and hole 42. Opening 34D is provided to allow medicament chamber 34B to communicate with the end of needle cartridge assembly 58 when barrel 36 is rotated by spring 46A when trigger 4 is activated. O-ring 34E is held in recess 34F to seal the medicament chamber and the end 58 of needle assembly 30 when the barrel 36 rotates to allow opening 34D to communicate with the end 58 of needle assembly 30.

Spring 23 is released by the action of lever 24 which is controlled by trigger 2. As the needle cartridge is extended by the action of spring 23, the end 58 of needle retainer element 44 is extended past the end of barrel 36 which allows barrel 36 to be axially rotated by the action of an axial spring 46A to cause vacuum cartridge 32 to move into register with off center hole 42 which is in communication with needle 18. As the vacuum cartridge tube 32 rotates into register with off center hole 42, a detent 35A in groove 34A stops rotary movement of the barrel 36. The vacuum cartridge 32 is opened to place a vacuum on needle 18 by opening end cap 60 and digitally depressing plunger element 47 against the force exerted by spring 45 to cause needle 45A to break the seal 32A on the vacuum in vacuum cartridge 32. The effect of the vacuum on the end of needle 18 is to aspirate any fluid in the tympanic cavity or middle ear.

The vacuum cartridge 32 and the medicament chamber 34 are within barrel 36. The vacuum cartridge is preferably provided with a vacuum which may be approximately $P<5\times10^{-3}$ Pa.

Figure 3:
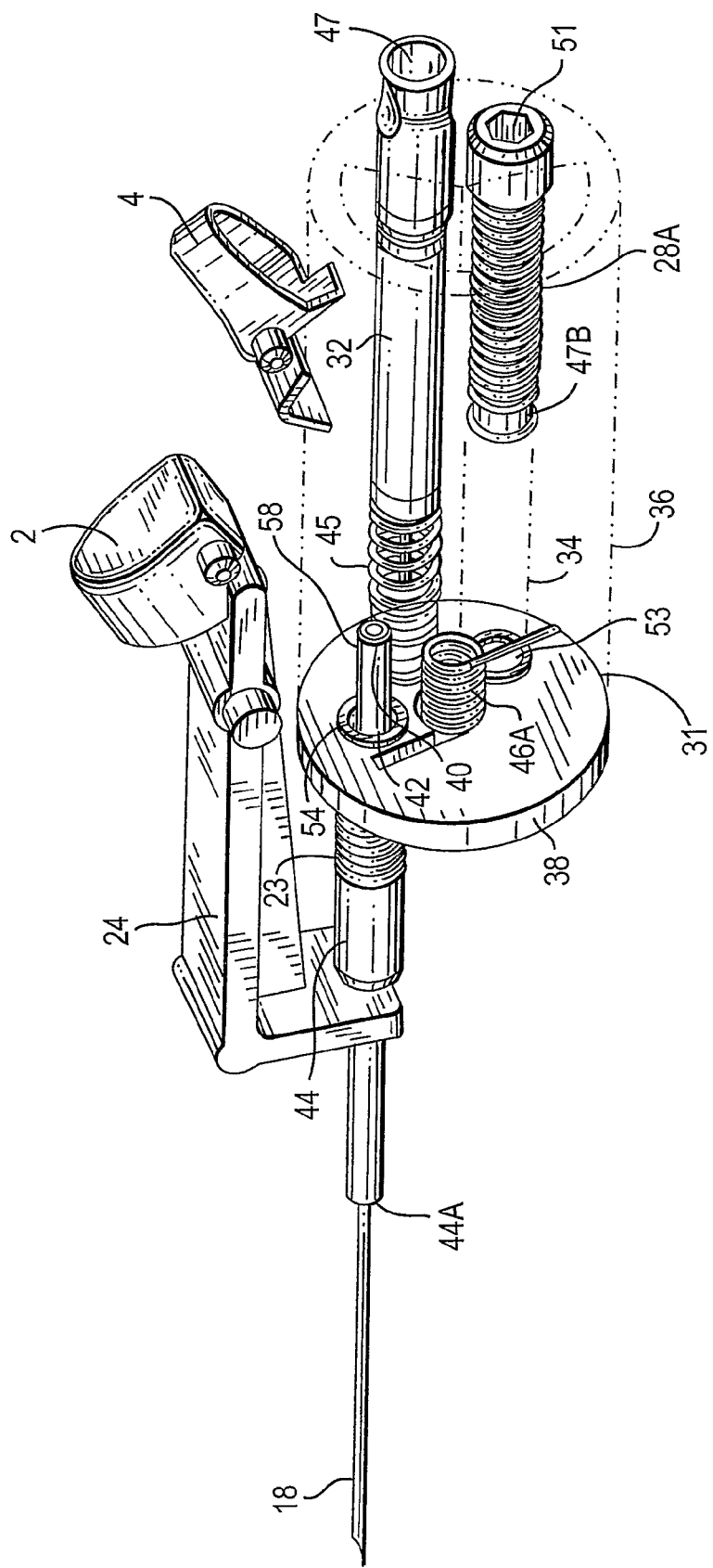
FIG. 3 is a rear perspective view of some of the operating parts that fit within the internal portion of the barrel shown in FIG. 2.
Figure 5:
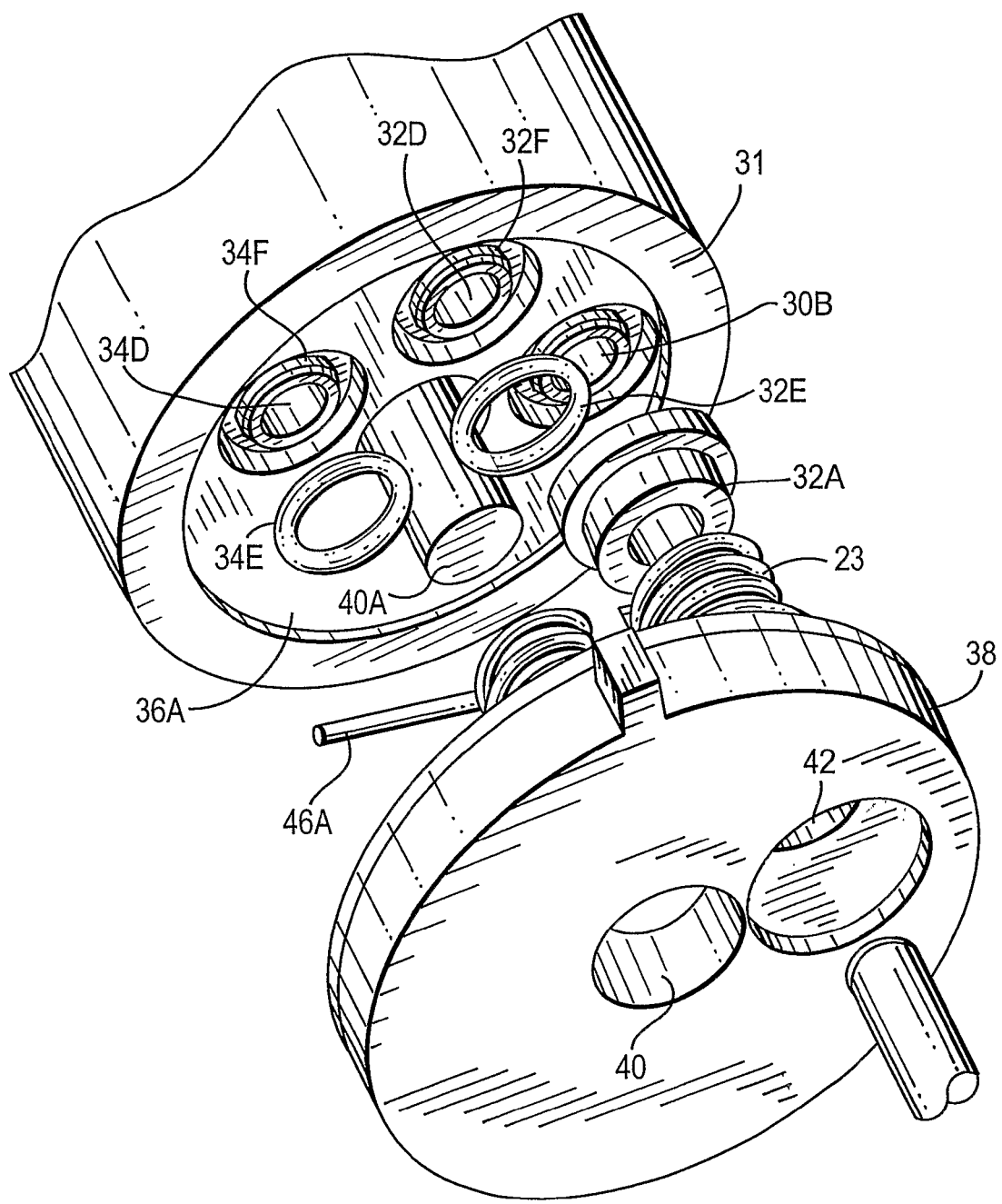
FIG. 5 is a partially exploded view of the end of the barrel assembly of the device of the invention.

As best seen in FIG. 5, turret 38 is provided with axial hole 40 and off center hole 42. The barrel 36 rotates due to the action of axial spring 46A to bring the vacuum cartridge 32 into register with off center hole 42. The vacuum cartridge 32 is provided with a constricted end portion 48. This constricted end portion 48 engages off center hole 42 when the vacuum cartridge contacts the off center hole 42A. A small needle 45A in constricted end portion 48 which is mounted at the end of vacuum tube 32 breaks the vacuum seal 32C as plunger element 47 is manually depressed. O-ring 46B is mounted inside of barrel 36 to seal the end of vacuum cartridge 32 against the inside of opening 32D. Spring 45 is held in recess 54 as shown in FIG. 3 on the inner side of offset hole 42 so that it does not move out of alignment with offset hole 42. The end 58 of needle retainer element 44 is adapted to rotate so that it is centered on O-ring 32E in back of spring retainer 32A. Needle 18 is attached to the end of needle retainer element 44A which forms a conduit from the tip of needle 18 to end 58. Expanded mid-section of needle retainer element 44 cooperates with retainer stop 46C to prevent end of needle retainer element 58 from being extended beyond the end of turret 38 by the action of spring 23. Thus, in operation, as needle cartridge assembly 30 is extended from barrel 36 by the action of spring 23, the action of the axial spring 46A on barrel 36 causes the barrel 36 to rotate until it reaches a detent 35A set in groove 34A where trigger 4 extension 4A causes the rotary movement of the barrel to stop and which causes the vacuum tube 32 to be held in register with offset hole 42. As described above, digital pressure is used to break the vacuum seal with needle 45A to cause the seal on said vacuum cartridge 32 to open and expose the tympanic cavity or middle ear to the vacuum in the vacuum cartridge which is sufficient to extract any fluid from behind the tympanic membrane through needle 18 without damaging any of the inner ear tissues.

As best seen in FIG. 3, medicament chamber 34 is shown by dotted lines within barrel 36. The medicament chamber 34 is provided with a constricted end portion which acts as seal 47B.

Figure 4:
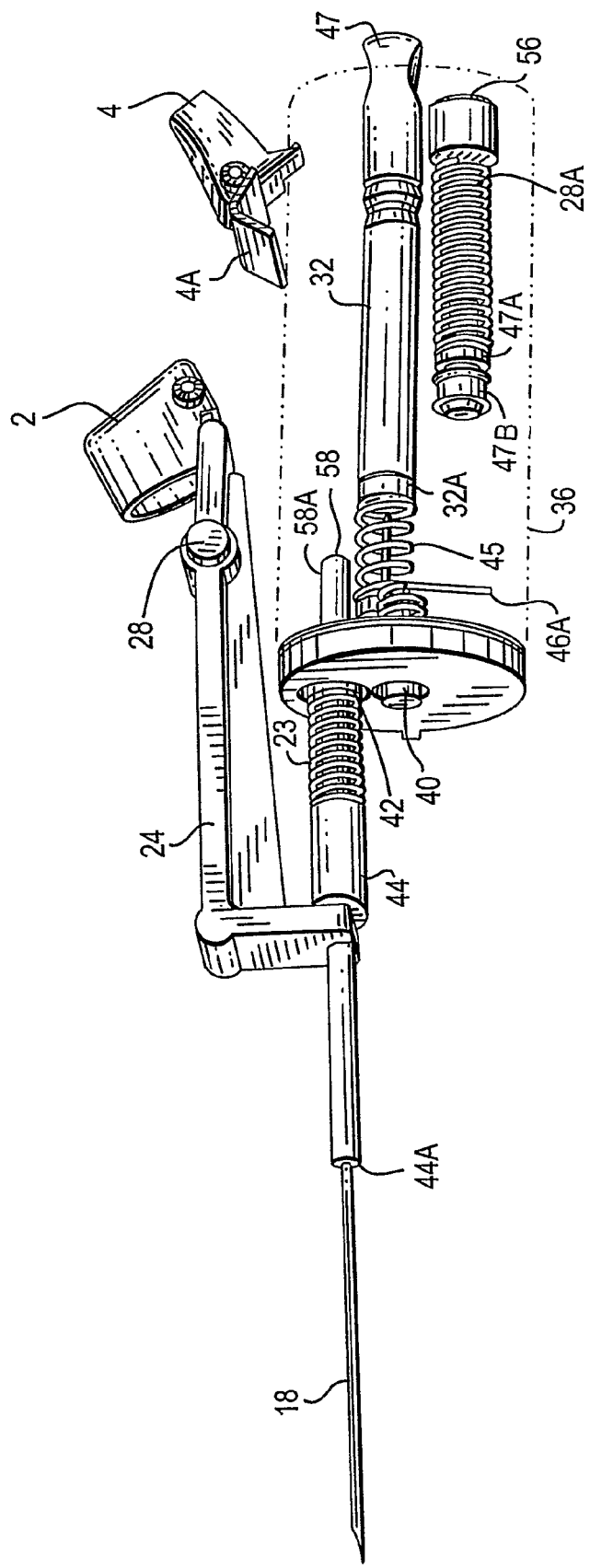
FIG. 4 is a front perspective view of some of the operating parts that fit within the internal portion of the barrel shown in FIG. 2.

As best seen in FIG. 4, spring retainer element 56 is positioned against spring 28A which contacts connector element 47A which contacts seal 47B in medicament chamber 34 in barrel 36. The medicament is stored in medicament chamber 34 between seal 47B and turret 38. When trigger 4 is activated, detent 35A is bypassed and barrel 36 rotates to allow medicament to be ejected, through needle 18 by the action of spring 28A on connector 47A and seal 47B, into the space behind the tympanic membrane.

Figure 6:
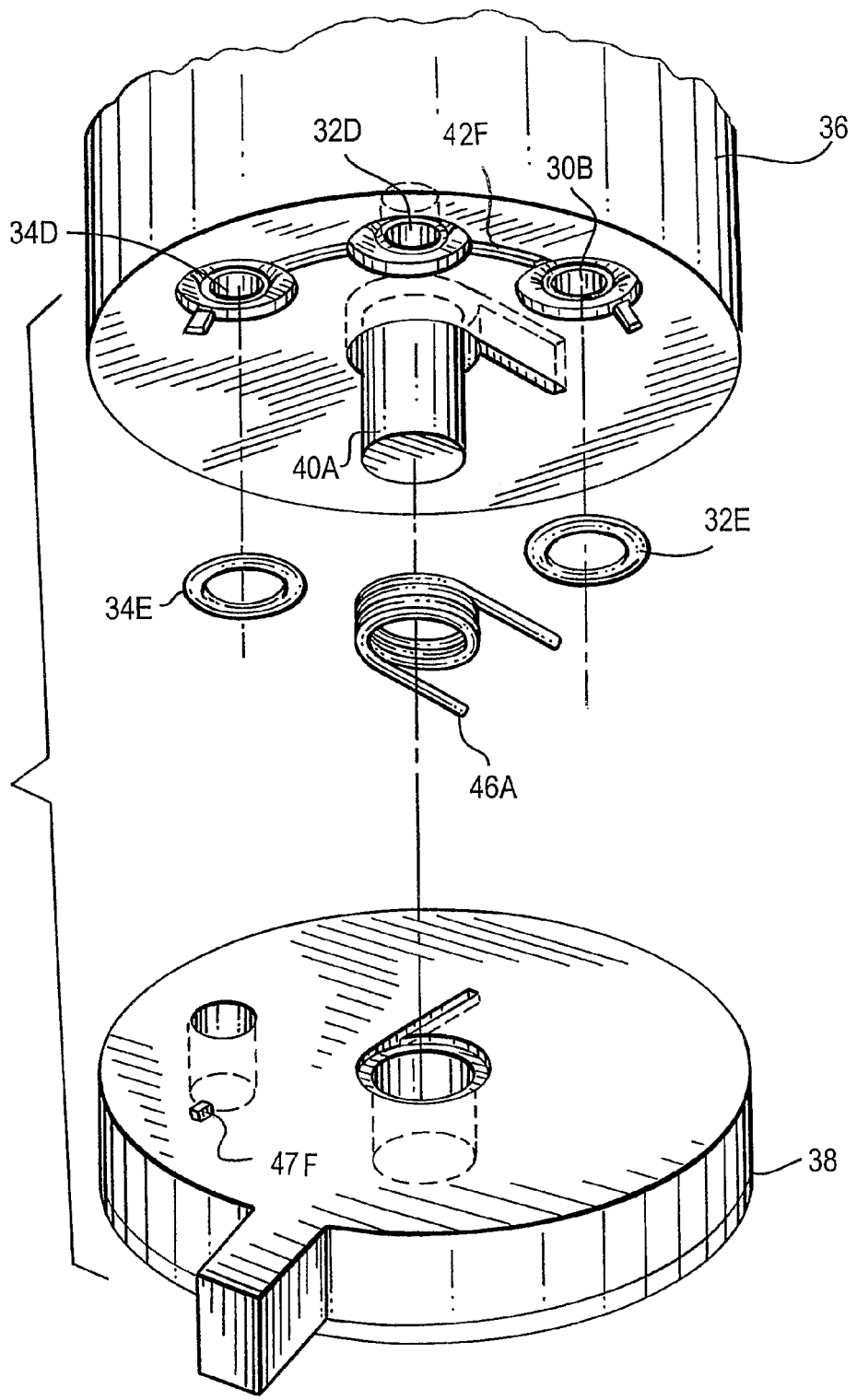
FIG. 6 is an exploded perspective view of the barrel and turret assembly which shows a sealed antibiotic chamber and a device for opening said antibiotic chamber.

As best shown in FIG. 6, the end of seal 47B in medicament chamber 34 may be ruptured by cutting element 47F on turret 36 as the barrel 38 rotates and passes over the end of the medicament chamber 34 under the action of a spring which is released by the trigger. Recessed channel 42F is provided in barrel 36 to allow cutting element 47F to move across the vacuum chamber and over the medicament chamber where it breaks seal 47B.

After medicament is injected into the middle ear and the device is removed from the patient's ear, vacuum cartridge 32 can be removed from barrel 36 for testing of effluent aspirated from the tympanic cavity or middle ear.

The apparatus of the invention including the needle cartridge, vacuum cartridge and medicament chamber are all manufactured so that they are sterile when delivered to the physician. Various procedures are well known for the preparation of pre-filled sterile applicators and for packaging these devices in suitable containers to maintain sterility.

The particular medicaments that may be provided in the medicament cartridge include antibiotics, anesthetics etc. which are disclosed above.

The invention claimed is:

1. A device for making an incision in the tympanic membrane, withdrawing fluid from the tympanic cavity or middle ear and administering a medicament to the tympanic cavity or middle ear, said device comprising a barrel shaped casing having a rotatable end turret adapted to engage tubular elements:
    (a) a first actuating trigger which activates a first tubular element in which is disposed a spring-loaded, hollow piercing shaft that is extendible from said barrel shaped casing said shaft having a first end which is adapted to penetrate a tympanic membrane when it is extended from said barrel shaped casing by the action of said spring and a second internal end which is adapted to engage an end of a tubular vacuum cartridge having a seal wherein the spring-loaded, hollow piercing shaft, having a first end which is adapted to penetrate a tympanic membrane when it is extended from said barrel shaped casing, has a stop on a second end that prevents said hollow piercing shaft from being extended beyond said turret;
    (b) said tubular vacuum cartridge having a seal, being positioned in said barrel shaped casing and having an axial spring for providing axial rotation in said barrel, when said hollow piercing shaft is completely extended from said barrel casing, said tubular vacuum cartridge having a seal, said vacuum cartridge being adapted to axially move into register with said second internal end of said piercing shaft to expose said hollow piercing element to the effect of vacuum in said tubular vacuum container in order to aspirate fluid from said tympanic cavity or middle ear;
    (c) a second actuating axial spring loaded tubular medicament chamber having a seal, which is positioned in said barrel casing and is adapted to rotate under the action of said second trigger and engage the second internal end of said piercing element and release medicament into the tympanic cavity or middle ear.

2. A device as claimed in claim 1 wherein (a) said first tubular element having the spring-loaded, hollow piercing shaft; (b) said tubular vacuum container; and (c) said medicament chamber are mounted in said barrel on an axially rotatable shaft disposed centrally in said barrel.

3. A device as claimed in claim 1 wherein the rotatable turret which has three openings which engage said (a) said first tubular element having the spring-loaded, hollow piercing shaft; (b) said tubular vacuum container; and (c) said medicament chamber.

4. A device as claimed in claim 3 wherein the rotatable turret which has three openings which engage said (a) said first tubular element having the spring-loaded, hollow piercing shaft; (b) said tubular vacuum cartridge; and (c) said tubular medicament cartridge include a seal between said turret which excludes any microbial contamination.

5. A device as claimed in claim 3 wherein the rotatable barrel has three tubular elements which engage (a) said first tubular element having the spring-loaded, hollow piercing shaft; (b) said tubular vacuum cartridge; and (c) said medicament chamber.

6. A device as claimed in claim 1 wherein the spring-loaded, hollow piercing shaft is adapted to act as a conduit for exposing the tympanic cavity or middle ear to a vacuum.

7. A device as claimed in claim 1 wherein the barrel has a spring for ejecting medicament from said medicament chamber.

8. A device as claimed in claim 1 including a housing which is adapted to engage an otoscope for direct viewing of the tympanic membrane as the spring loaded hollow piercing shaft is extended through the tympanic membrane.

9. A device as claimed in claim 4 wherein the seal comprise O-rings.

10. A method for administering a liquid medicament into the tympanic cavity or middle ear which comprises making an incision in the tympanic membrane, withdrawing fluid from the tympanic cavity or middle ear and administering a medicament to the tympanic cavity or middle ear by passing a hollow piercing shaft through the tympanic membrane by means of a device comprising a barrel shaped casing having a rotatable end turret adapted to engage tubular elements:
    (a) a first actuating trigger which activates a first tubular element in which is disposed a spring-loaded, hollow piercing shaft having a first end which is adapted to penetrate a tympanic membrane when it is extended from said barrel shaped casing by the action of said spring and a second internal end which is adapted to engage an end of a tubular vacuum cartridge having a seal;
    (b) said tubular vacuum cartridge having a seal, being positioned in said barrel shaped casing and having an axial spring for providing axial rotation in said barrel, when said hollow piercing shaft is completely extended from said barrel casing, said tubular vacuum cartridge having a seal, said vacuum cartridge being adapted to axially move into register with said second internal end of said piercing shaft to expose said hollow piercing element to the effect of vacuum in said tubular vacuum container in order to aspirate fluid from a space behind said tympanic membrane;
    (c) a second trigger actuating axial spring loaded medicament chamber having a seal, which is positioned in said barrel casing and is adapted to rotate under the action of said second trigger and engage the second internal end of said piercing element and release medicament into the tympanic cavity or middle ear.

11. A method for obtaining a specimen of fluid from the tympanic cavity or the middle ear which comprises making an incision in the tympanic membrane, withdrawing fluid from the tympanic cavity or middle ear which comprises passing a hollow piercing shaft through the tympanic membrane by means of a device comprising a barrel shaped casing having a rotatable end turret adapted to engage tubular elements:
    (a) a first actuating trigger which activates a first tubular element in which is disposed a spring-loaded, hollow piercing shaft having a first end which is adapted to penetrate a tympanic membrane when it is extended from said barrel shaped casing by the action of said spring and a second internal end which is adapted to engage an end of a tubular vacuum cartridge having a seal;
    (b) said tubular vacuum cartridge having a seal, being positioned in said barrel shaped casing and having an axial spring for providing axial rotation in said barrel, when said hollow piercing shaft is completely extended from said barrel casing, said tubular vacuum cartridge having a seal, said vacuum cartridge being adapted to axially move into register with said second internal end of said piercing shaft to expose said hollow piercing element to the effect of vacuum in said tubular vacuum container in order to aspirate fluid from a space behind said tympanic membrane; and (c) recovering said fluid from said tubular vacuum chamber.

* * * * *